(12) United States Patent
Coppi et al.

(10) Patent No.: US 6,967,248 B2
(45) Date of Patent: Nov. 22, 2005

(54) CRYSTALLINE FORMS OF MELOXICAM AND PROCESSES FOR THEIR PREPARATION AND INTERCONVERSION

(75) Inventors: Laura Coppi, Barcelona (ES); Marti Bartra Sanmarti, Barcelona (ES); Montserrat Closa Clavo, Barcelona (ES)

(73) Assignee: Esteve Quimica, SA, Barcelona (ES)

( * ) Notice: Subject to any disclaimer, the term of this patent is extended or adjusted under 35 U.S.C. 154(b) by 298 days.

(21) Appl. No.: 10/314,542

(22) Filed: Dec. 9, 2002

(65) Prior Publication Data

US 2003/0109701 A1 Jun. 12, 2003

(30) Foreign Application Priority Data

Dec. 11, 2001 (ES) .......................................... 200102743

(51) Int. Cl.$^7$ ............................................. C07D 417/12
(52) U.S. Cl. .................................................... 544/49
(58) Field of Search ........................................... 544/49

(56) References Cited

U.S. PATENT DOCUMENTS 4,233,299 A * 11/1980 Trummlitz et al. ...... 514/226.5

FOREIGN PATENT DOCUMENTS

DE  27 56 113  12/1977

OTHER PUBLICATIONS

Xu, You–Jun; Liu, Feng; Yang, Zhi–Min, Hecheng Huaxue, 7(2), 118–120 (English) 1999.*

Lazer, Edward S.; et al Journal of Medicinal Chemistry, 40(6), 980–989 (English) 1997.*

Luger, P. et al, Eur. J. Pharm. Sci., 4(3) 175–187.*

Lara Ochoa, Jose Manuel Francisco; et al cited in Chemical Abstracts 2003:711263, Lara Ochoa, Jose Manuel Francisco; et al Mex. Pat. Appl. MX 9908522 A 20000228.*

* cited by examiner

*Primary Examiner*—Thomas C. McKenzie
(74) *Attorney, Agent, or Firm*—Katten Muchin Zavis Rosenman

(57) ABSTRACT

The invention relates to the new crystalline forms II, III and V of meloxicam; to the processes for obtaining the crystalline forms I, II, III and V; and, finally, to the interconversion processes of the forms II, III, IV and V into the form I.

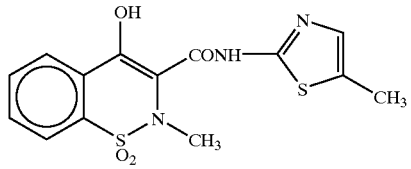

33 Claims, 14 Drawing Sheets

FIG.5 IR SPECTRUM OF MELOXICAM FORM V

X-RAY DIFFRACTOGRAM OF MELOXICAM FORM II

CRYSTALLINE FORMS OF MELOXICAM AND PROCESSES FOR THEIR PREPARATION AND INTERCONVERSION

FIELD OF THE INVENTION

The present invention relates to the crystalline forms of meloxicam and to processes for their preparation and interconversion. More specifically, it relates to the new crystalline forms II, III and V of meloxicam; to the processes for obtaining said new crystalline forms II, III and V; and finally, to the processes for interconverting the forms II, III, IV and V into the form I.

BACKGROUND OF THE INVENTION

Meloxicam, 4-hydroxy-2-methyl-N-(5-methyl-2-thiazolyl)-2H-1,2-benzothiazine-3-carboxamide 1,1-dioxide, is a known non-steroid anti-inflammatory drug (NSAID). Standard NSAID's inhibit both the isoform COX-1 of cyclooxygenase, that is constitutively expressed in many tissues, and the isoform COX-2, that is expressed as a response to inflammatory mediators. Although current NSAID's present certain differences in potency as inhibitors of these two enzymes, they generally inhibit both. From a theoretical standpoint at least it would therefore be advantageous to inhibit selectively COX-2 (reducing the inflammation) without affecting COX-1 (thereby leaving intact this enzyme, and thus reducing possible kidney and gastric damage). The importance of meloxicam in the pharmaceutical field is given by the fact that this compound selectively inhibits COX-2 instead of COX-1. Thus, meloxicam shows a selectivity that is 75 times greater for COX-2 compared to COX-1, in human recombinant enzymes. (Churchil L, Graham A C, Shih C-K, et al. Selective inhibition of human cyclooxygenase-2 by meloxicam. Inflammopharmacology, 1996; 4: 125–135).

It is known that meloxicam shows polymorphism, with two different crystalline forms known: the zwiterionic form (hereinafter referred to as form IV) and the enolic form, or form I. The crystalline form I is the one suitable for preparing pharmaceutical products (P. Luger et al. Eur. J. Pharm. Sci., 1996, 175).

Enolic form, or form I, of meloxicam (Formula A):

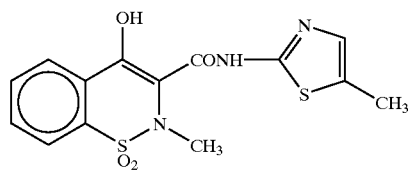

Zwiterionic form, or form IV, of meloxicam (Formula B):

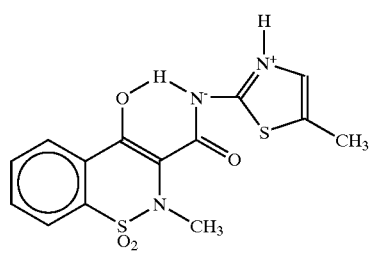

In the current state of the art, meloxicam is obtained by reacting isopropyl 4-hydroxy-2-methyl-2H-1,2-benzothiazine-3-carboxylate 1,1-dioxide (or other derivatives of carboxylic acid) and 2-amino-5-methylthiazol in xylene at reflux with partial distillation. The meloxicam thus obtained must be purified for adequate quality. Said purification is performed by crystallisation in organic solvents such as dichloroethane or 1,2-dichlorobenzene (see DE 2756113). The paper by P. Luger et al. Eur. J. Pharm. Sci., 1996, 175 describes the preparation of meloxicam, characterised as form I, by recrystallisation in non-polar solvents. This same document describes the preparation of the form IV or zwiterionic form by treating meloxicam in an aqueous medium with soda followed by acetic acid.

The methods for obtaining the form I of meloxicam have the disadvantage of relying on organic solvents. This means that, in addition to the high cost of the solvent, it must be later eliminated and/or recovered. In addition, yields obtained by these crystallisation methods are moderate or relatively low (<75%).

These documents do not discuss the possibility of interconverting the form IV into the form I, nor the temperature and time used in the crystallisations. They also do not describe the possibility of directly obtaining the form I in an aqueous medium by treatment with soda and acetic acid.

Thus, there is a need for a method for preparing the form I of meloxicam that does not suffer from the drawbacks of known methods, as well as of new crystalline forms that serve as intermediates or starting products for preparing the form I of meloxicam and, finally, of processes for preparing said crystalline forms.

SUMMARY OF THE INVENTION

Through exhaustive and laborious research the inventors have developed a method by which, surprisingly, the form I of meloxicam can be obtained with excellent yields by crystallisation of meloxicam in an aqueous medium, a medium hitherto described for obtaining the form IV. This implies an advantage over previous methods as it avoids using organic solvents, which imply a need of additional installations as well as harming the environment. This method also provides a suitable process for purification of meloxicam. Thus, an aspect of the present invention is a method for obtaining and purifying meloxicam of form I from meloxicam.

A second aspect of the invention consists of new crystalline forms of meloxicam, named forms II, III and V, as well as the processes for preparation thereof. These crystalline forms can serve as intermediates or pure starting products for preparing the form I, or even open paths for preparation of new pharmaceutical formulations of meloxicam.

Finally, the inventors have developed processes allowing to convert the crystalline forms II, III, IV and V of meloxicam into the form I. This is thus the third aspect of the invention. These processes allow transforming the various crystalline forms of meloxicam into the form I, which is the form currently used in pharmaceutical preparations of meloxicam.

BRIEF DESCRIPTION OF THE DRAWINGS

The present descriptive memory has 14 figures.

DETAILED DESCRIPTION OF THE INVENTION

As mentioned above, the first aspect of the present invention consists of a method for preparing meloxicam form I, represented by the Formula A,

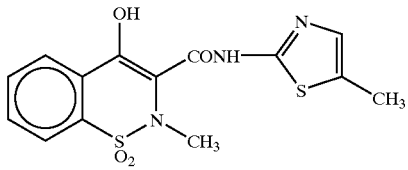

The first aspect of the invention consists of a method for preparing the crystalline form I of meloxicam, involving dissolving meloxicam in a mixture of water and NaOH, and the subsequent addition of an acid for precipitating the crystalline form I of meloxicam, maintaining during the process a temperature between 65° C. and the reflux temperature.

Throughout the application document the term meloxicam refers to the crude product obtained in any of the reactions for preparing said compound known in the state of the art; for example, by reacting isopropyl 4-hydroxy-2-methyl-2H-1,2-benzothiazine-3-carboxylate 1,1-dioxide (or other derivatives of carboxylic acid) and 2-amino-5-methylthiazol in xylene at reflux with partial distillation.

The acid used in the reaction of the first aspect of the invention can be an organic or inorganic acid, preferably hydrochloric, acetic or methansulphonic acid, and more preferably acetic acid. The acid is preferably added until reaching a pH of 3 to 5.5. The temperature of such process, with the exception of the crystallisation stage, is maintained between 65° C. and the reflux temperature, preferably between 65° C. and 80° C., and more preferably at 65° C., 80° C. or 100° C. The amount of NaOH added is preferably 1 to 1.5 equivalents of NaOH with respect to meloxicam.

Within the first aspect of the invention is a variation of the previous method, in which the meloxicam is dissolved in a mixture of water, NaOH and an organic solvent chosen form among: an alcohol, such as for example ethanol, xylene, toluene and dimethylformamide (DMF), and at a temperature that is maintained throughout the process between 50° C. and the reflux temperature.

The acid used, as in the previous process, is an organic or inorganic acid, preferably hydrochloric, acetic or methansulphonic acid, and more preferably acetic acid. The acid is preferably added until reaching a pH of 3 to 5.5. Preferred mixtures of solvents are: water/xylene 12.5:1 (v/v), water/DMF (v/v) between 1:1 and 8:1 and, finally, water/ethanol (v/v) between 10:1 and 1:1. The process temperature, with the exception of the precipitation stage, is preferably between 50 and 80° C., more preferably 50° C., 63° C. or 70° C. The amount of NaOH added is preferably 1 to 1.5 equivalents of NaOH with respect to meloxicam.

As mentioned above, the second aspect of the invention are new crystalline forms of meloxicam, denominated forms II, III and V, as well as the processes for preparing them.

Figure 1:
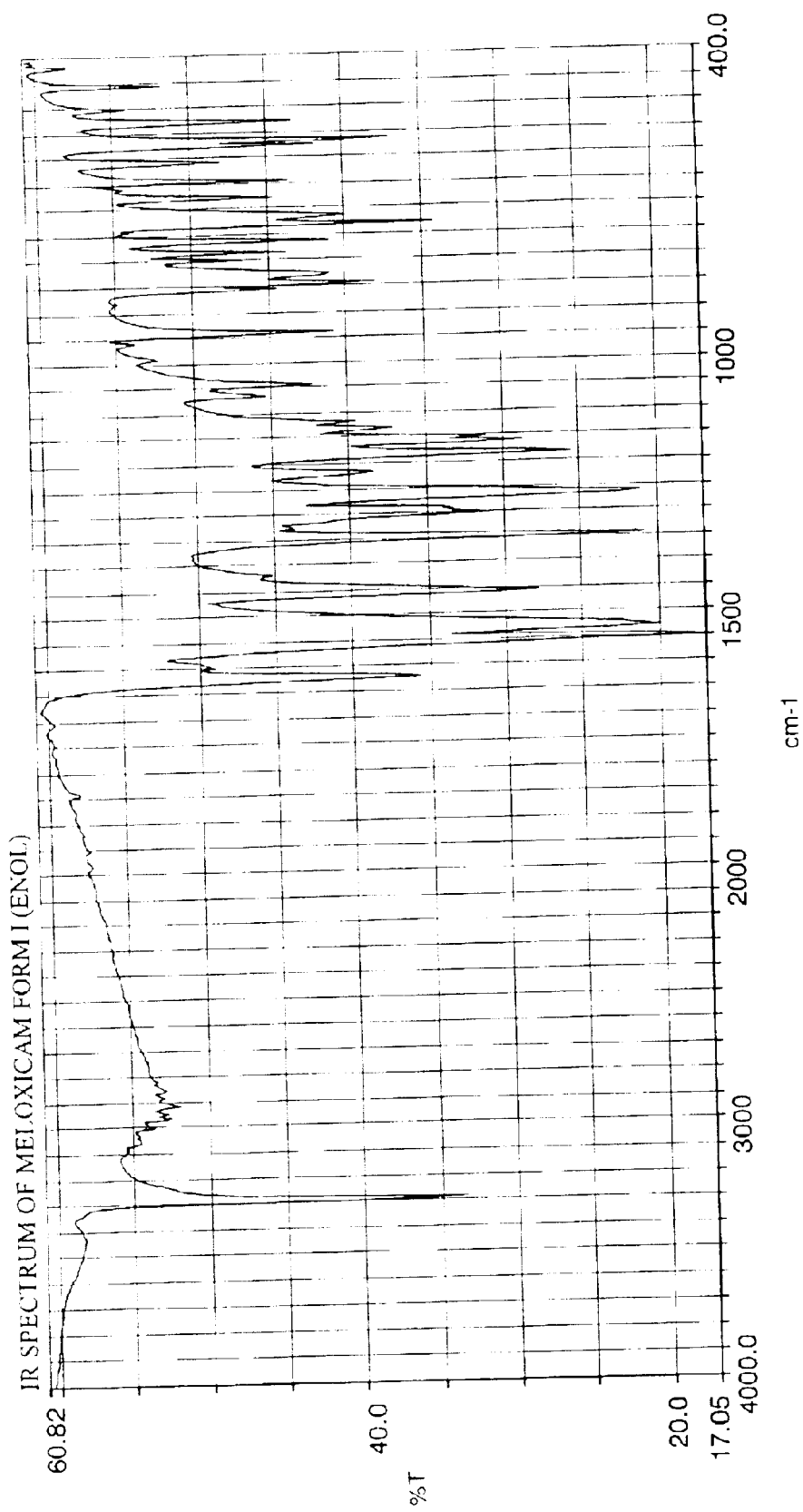
FIGS. 1, 2, 3, 4 and 5 show the infrared spectra of the crystalline forms I, II, III, IV and V of meloxicam.
Figure 2:
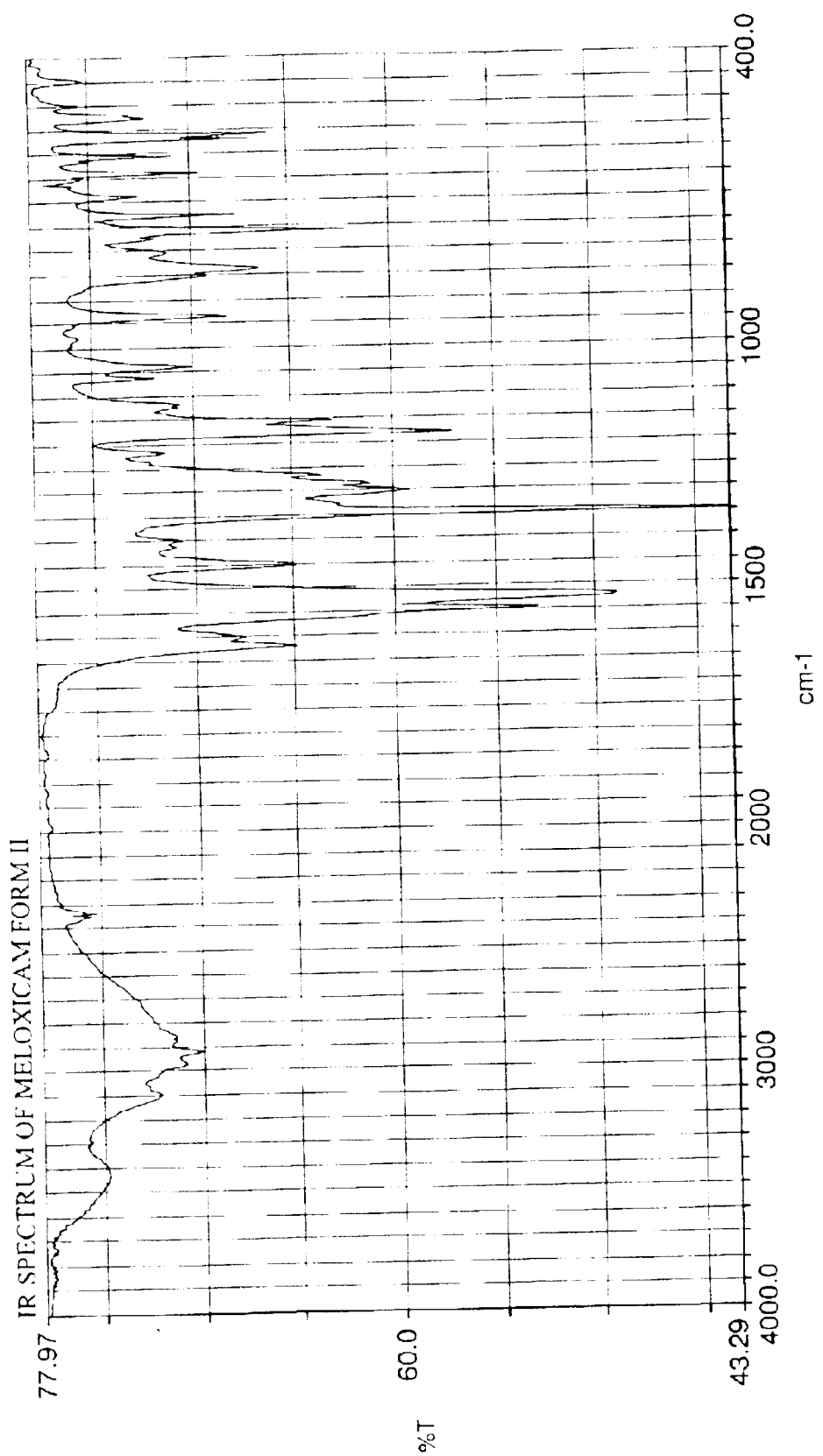
Figure 7:
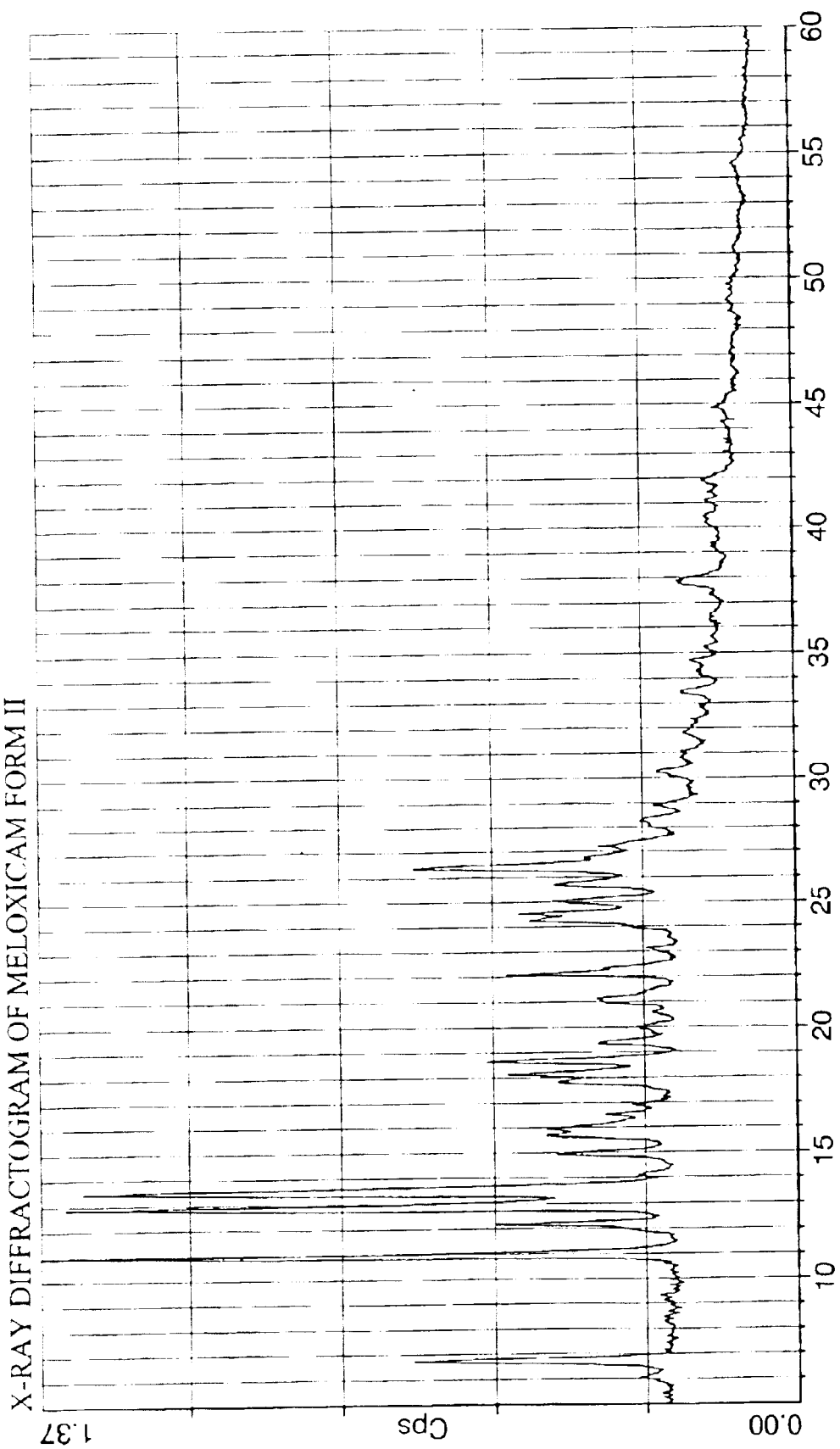

The crystalline form II of meloxicam is characterised by the following values of its infrared spectrum (see FIG. 2):

IR (KBr): v 3104, 2974, 2927, 2880, 2858, 1620, 1603, 1549, 1523, 1455, 1417, 1403, 1349, 1303, 1289, 1270, 1240, 1221, 1182, 1156, 1127, 1119, 1066, 1042, 939, 856, 842, 807, 779, 762, 731, 693, 644, 609, 574, 565, 531, 504, 454 cm$^{-1}$;

by the following values of its Raman spectrum (see FIGS. 11–14):

20 (vs), 31 (s), 73 (m), 100 (s), 371 (m), 407 (s), 506 (m), 646 (m), 668 (m), 1121 (s), 1128 (sh), 1155 (s), 1161 (s), 1267 (s), 1310 (vs), 1333 (vs), 1347 (vs), 1359 (vs), 1438 (s), 1476 (s), 1538 (vs), 1557 (vs), 1595 (vs), 1611 (vs); and by the X/ray diffractogram of FIG. 7.

The method for preparation of the crystalline form II of meloxicam involves carrying out the following stages:
 a) dissolving meloxicam in a mixture of water and NaOH at 45–50° C., with water/meloxicam (v(ml)/p(g)) ratio of 30 to 35,
 b) adding an acid until obtaining a pH of 3–5.5, maintaining the temperature of stage a),
 c) maintaining the suspension at the temperature of stage a) for 30 to 90 minutes, preferably 60 minutes, and
 d) cooling and isolating the precipitate.

The mixture of water and NaOH used in stage a) of the method for preparing the crystalline form II of meloxicam contains preferably 1 to 1.5 equivalents of NaOH with respect to meloxicam. The acid added in stage b) is preferably acetic acid.

Figure 3:
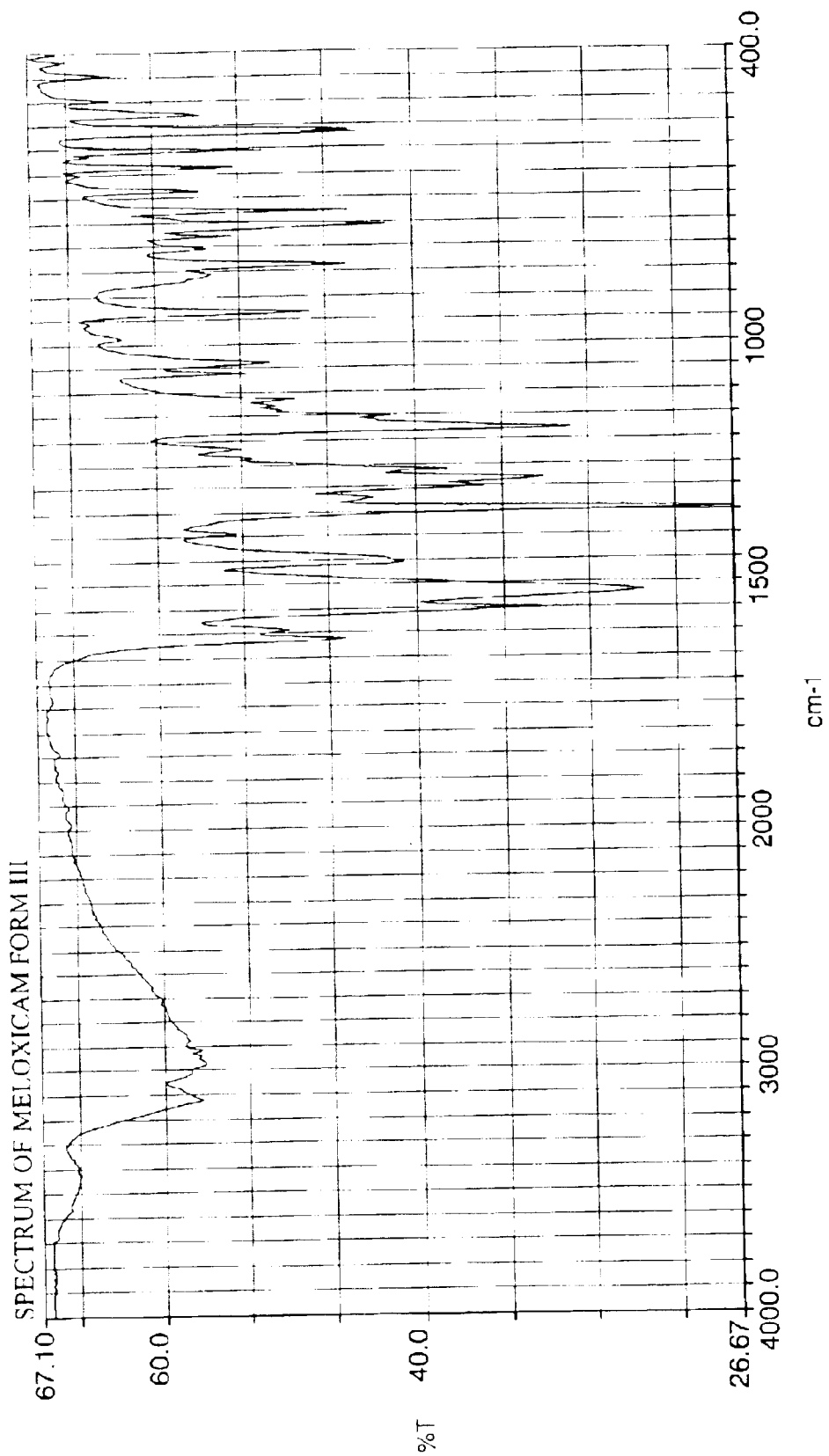
Figure 4:
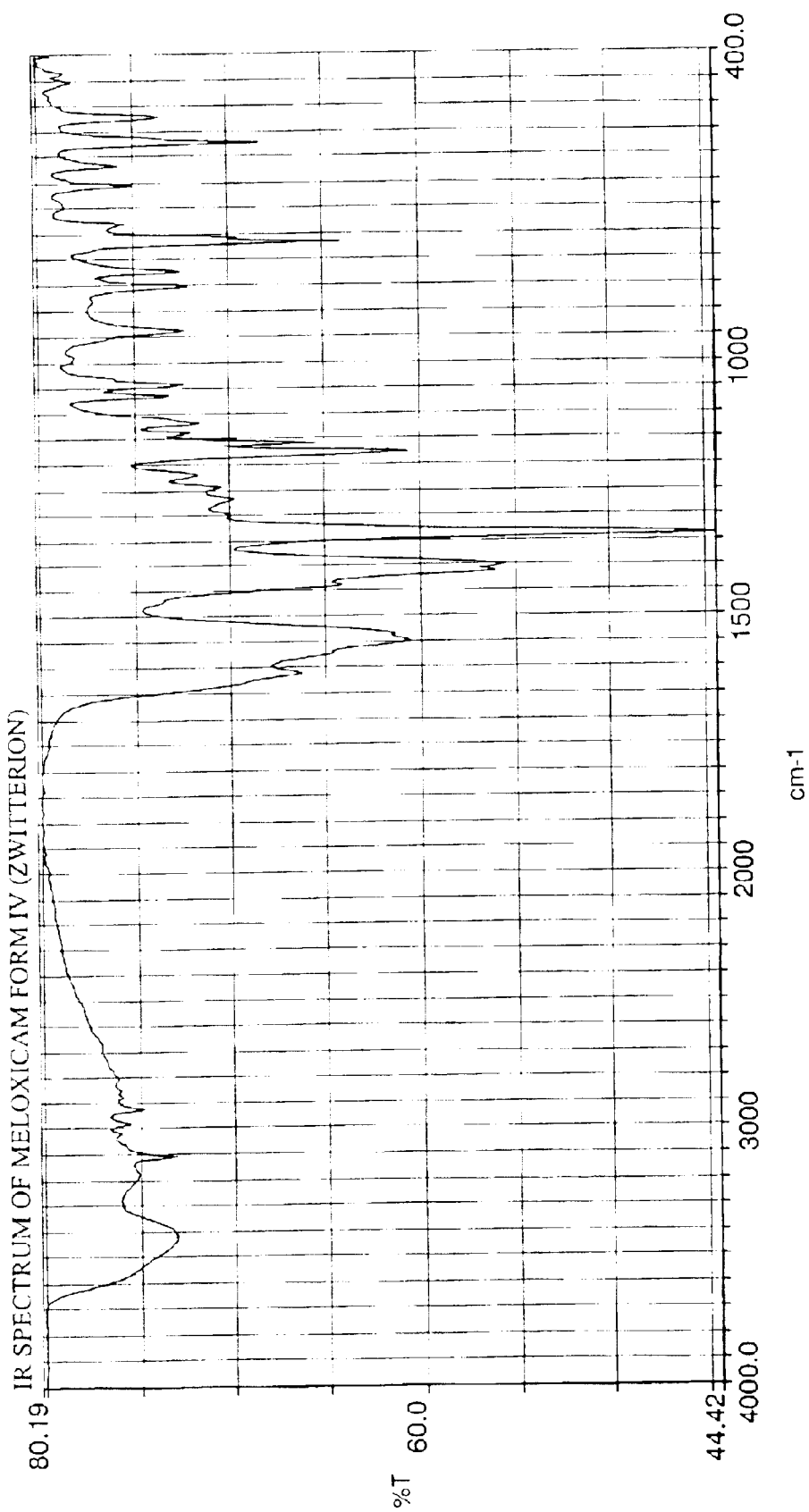
Figure 8:
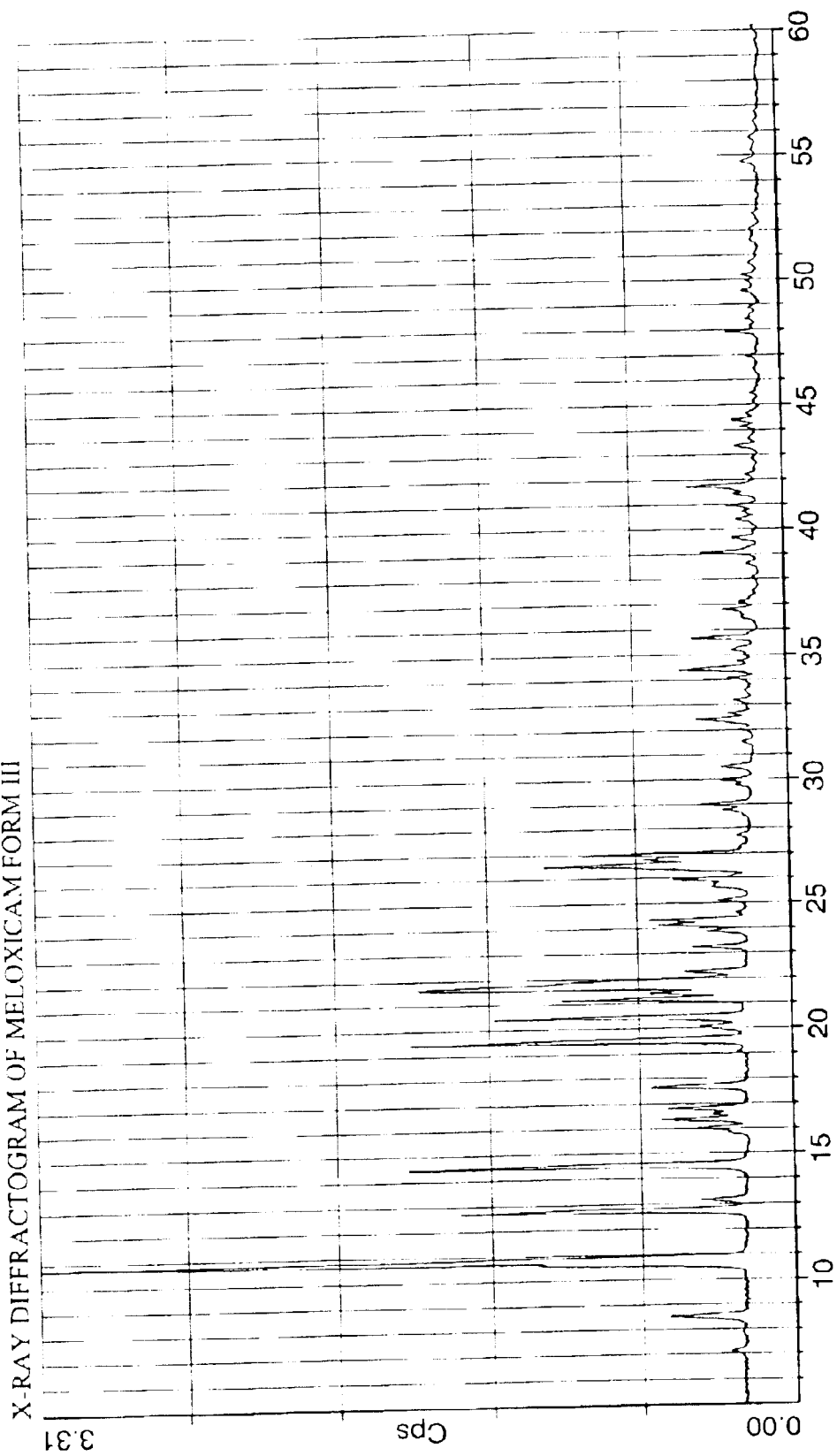
Figure 9:
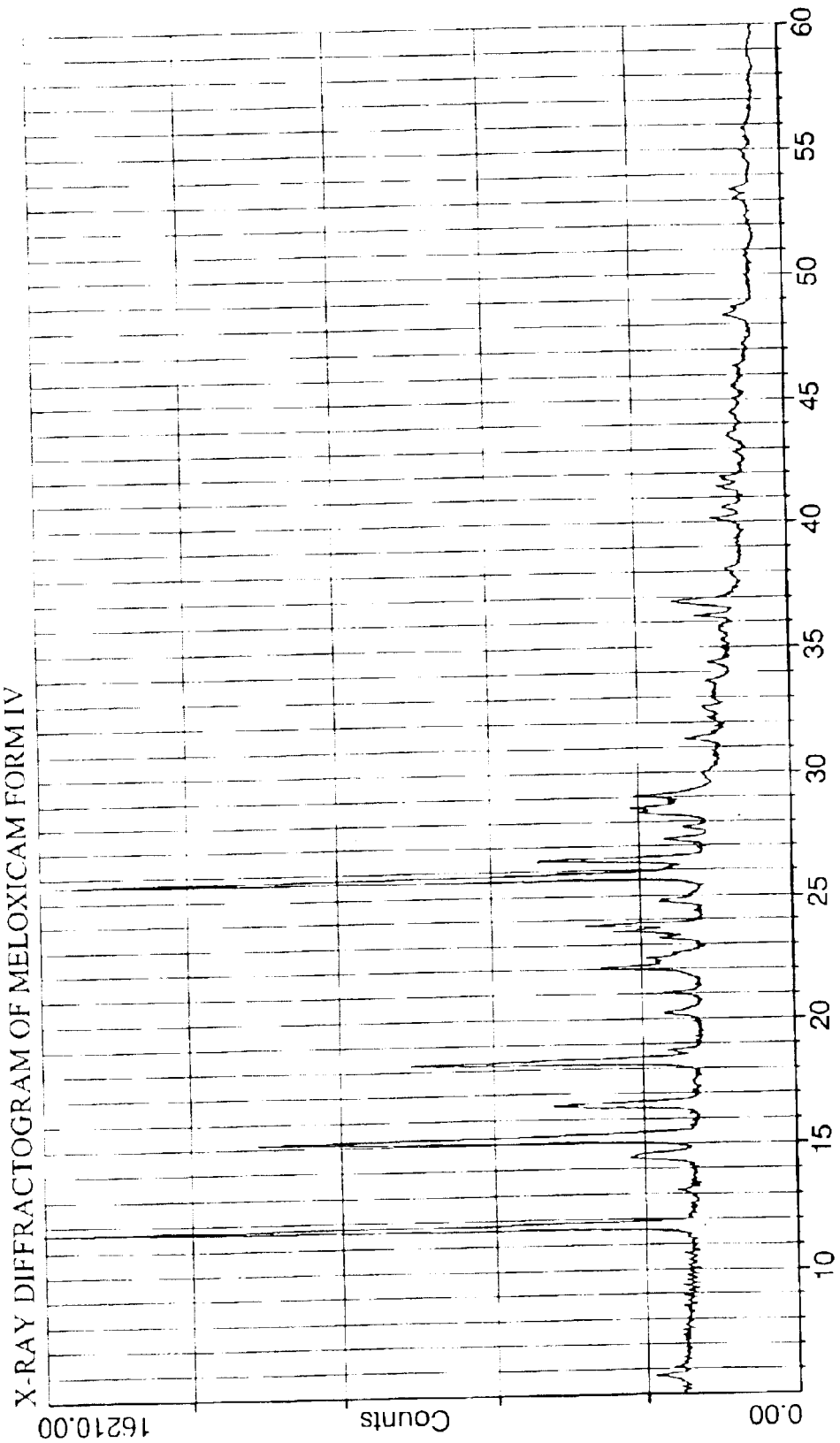

The crystalline form III of meloxicam is characterised by the following values of its infrared spectrum (see FIG. 3):

IR (KBr): v 3128, 2979, 2944, 2921, 1615, 1595, 1552, 1518, 1457, 1396, 1348, 1324, 1301, 1285, 1264, 1237, 1220, 1181, 1152, 1140, 1130, 1118, 1064, 1043, 992, 937, 860, 840, 807, 781, 758, 730, 688, 641, 607, 573, 565, 533, 523, 502, 454 cm$^{-1}$;

by the following values of its Raman spectrum (see FIGS. 11–14):

27 (s), 37 (s), 48 (s), 63 (s), 97 (m), 407 (s), 1119 (m), 1159 (m), 1261 (m), 1309 (s), 1323 (vs), 1357 (s), 1540 (vs), 1595 (vs);
and by the X-ray diffractogram of FIG. 8.

The method for preparing the crystalline form III of meloxicam involves the following stages:
 a) dissolving meloxicam in a mixture of water, NaOH and xylene at 45–50° C., with a concentration of meloxicam from 15 to 20 ml of water/g of meloxicam and with the concentration of xylene being from 5 to 10% by weight with respect to meloxicam,
 b) adding an acid for 30 to 90 minutes until obtaining a pH of 3–5.5, maintaining the temperature of stage a), and
 c) cooling and isolating the precipitate.

The mixture of water, NaOH and xylene used in stage a) of the method for preparation of the form III of meloxicam preferably includes 1 to 1.5 equivalents of NaOH with respect to meloxicam. The acid added in stage b) is preferably acetic acid.

Figure 5:
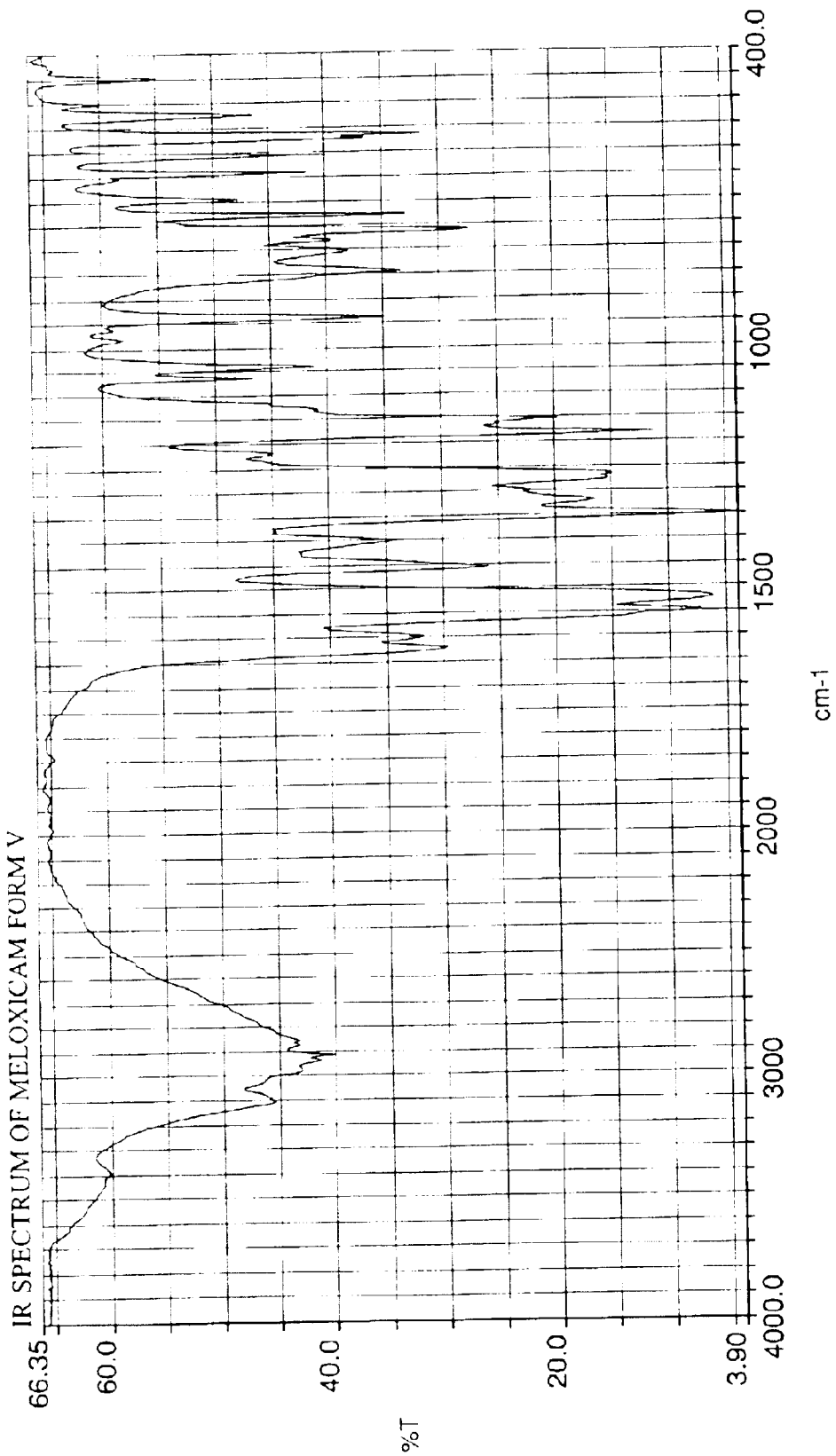
Figure 6:
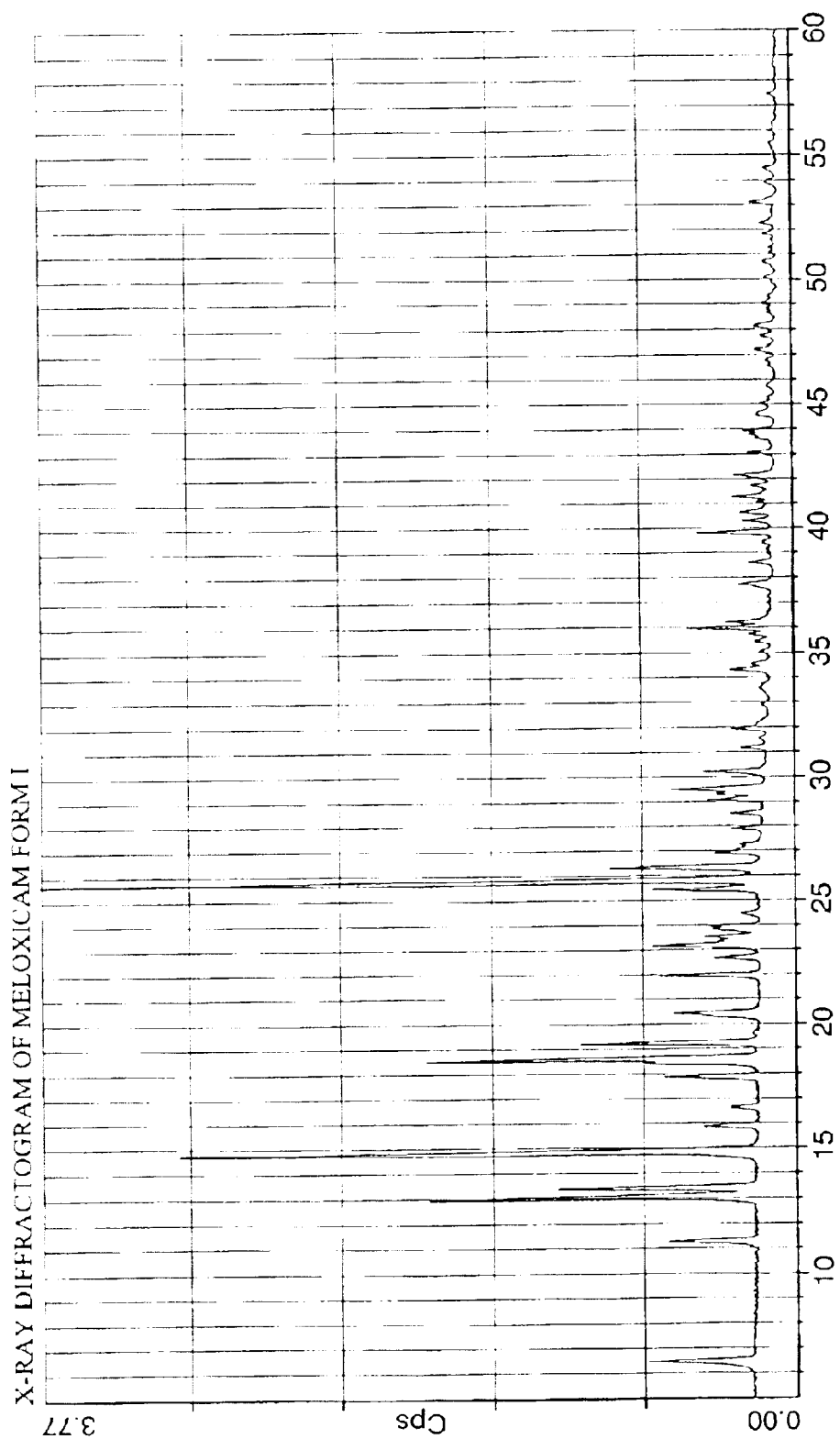
FIGS. 6, 7, 8, 9 and 10 show the X-ray diffractograms of the crystalline forms I, II, III, IV and V of meloxicam. Finally.
Figure 10:
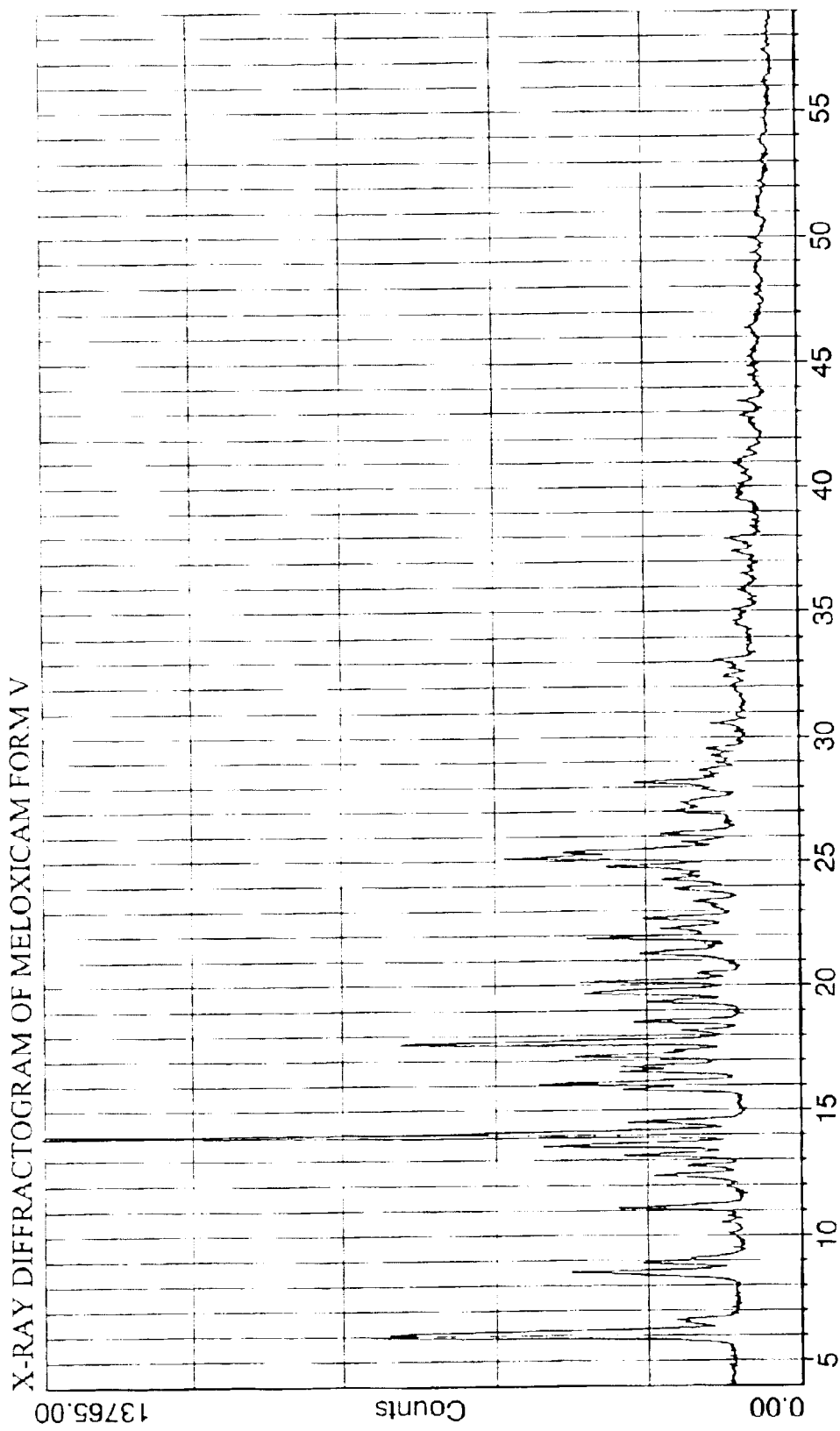
Figure 11:
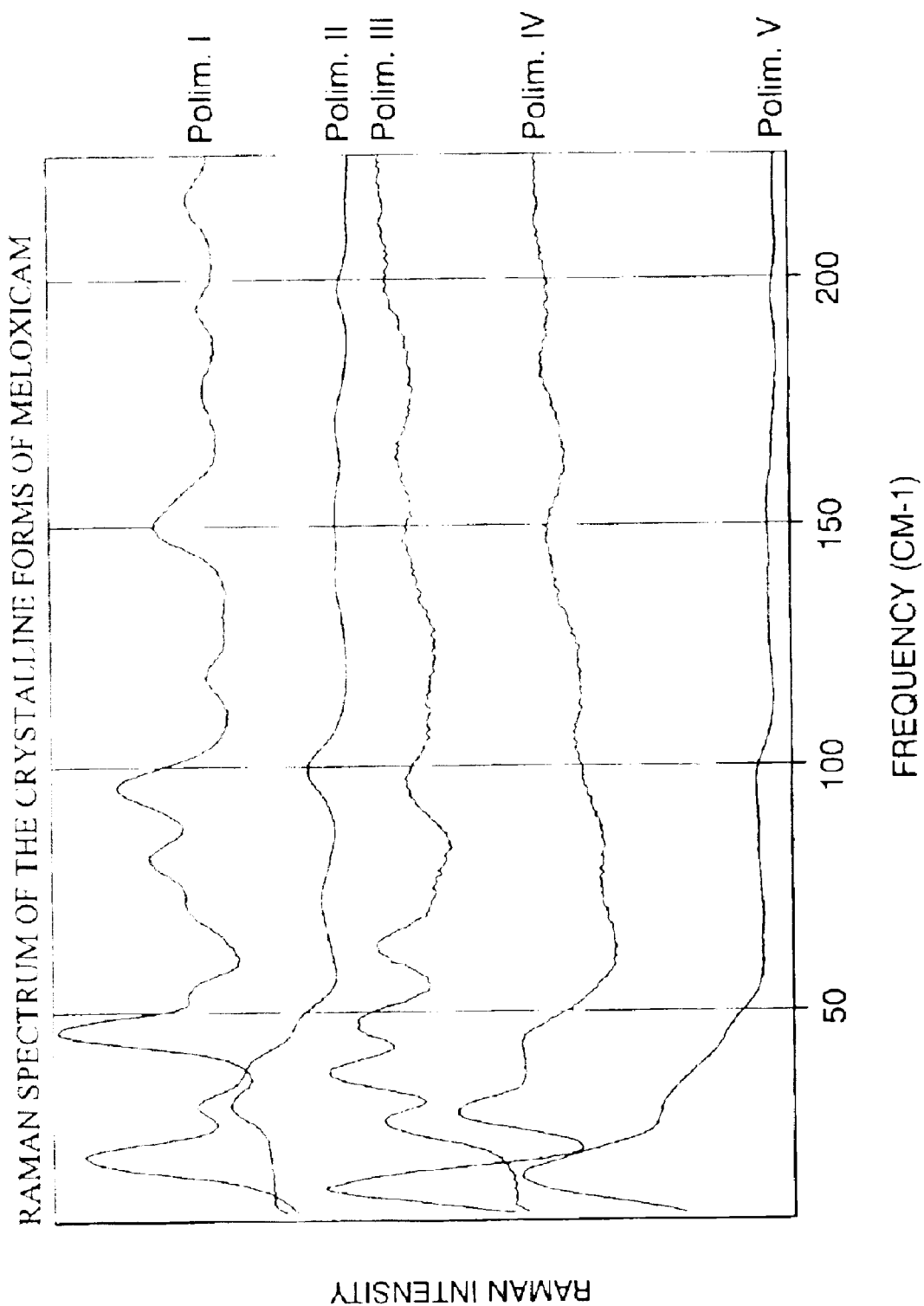
FIGS. 11, 12, 13, and 14 show the Raman spectra of the crystalline forms I, II, III, IV and V of meloxicam.
Figure 12:
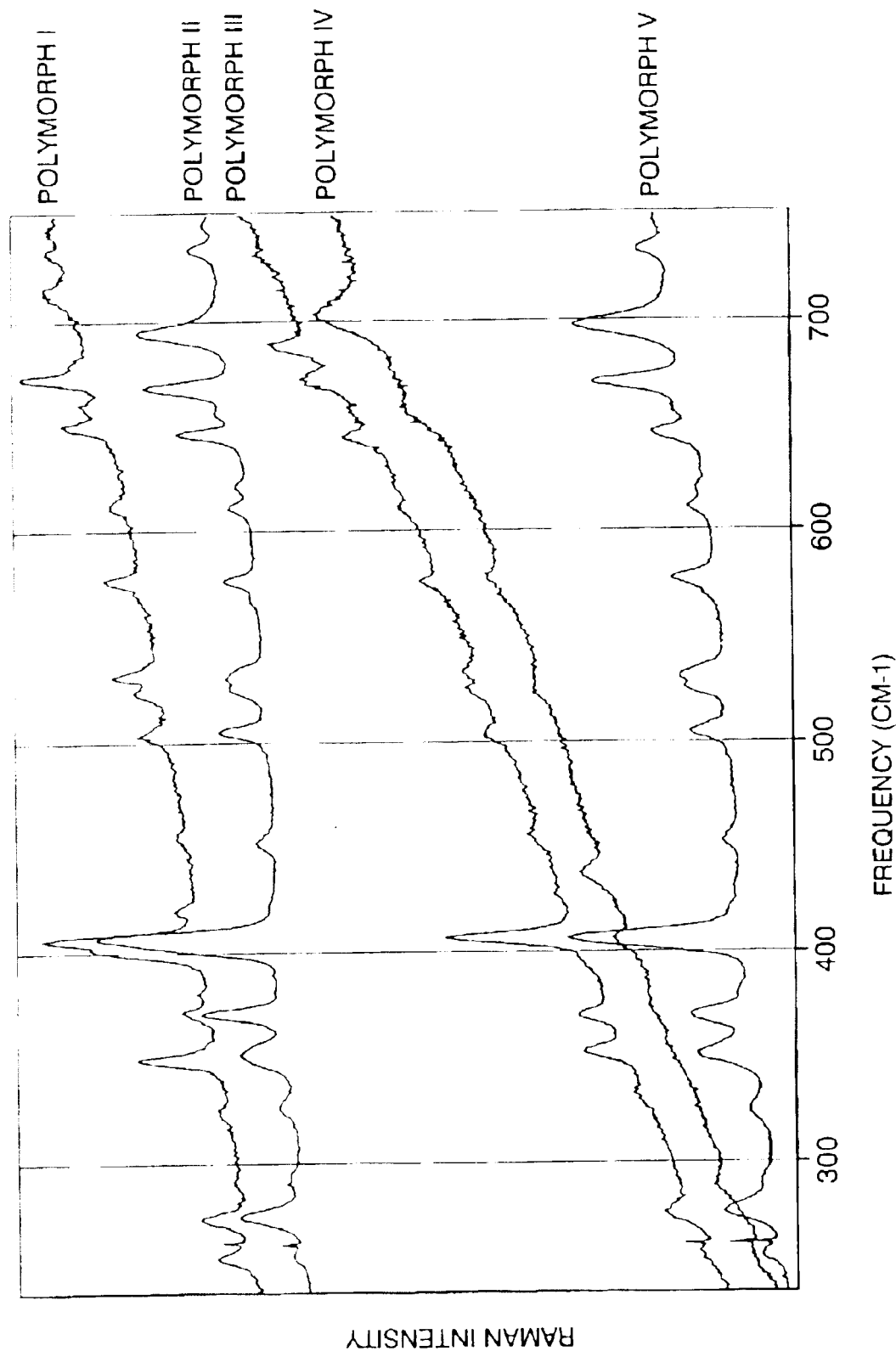
Figure 13:
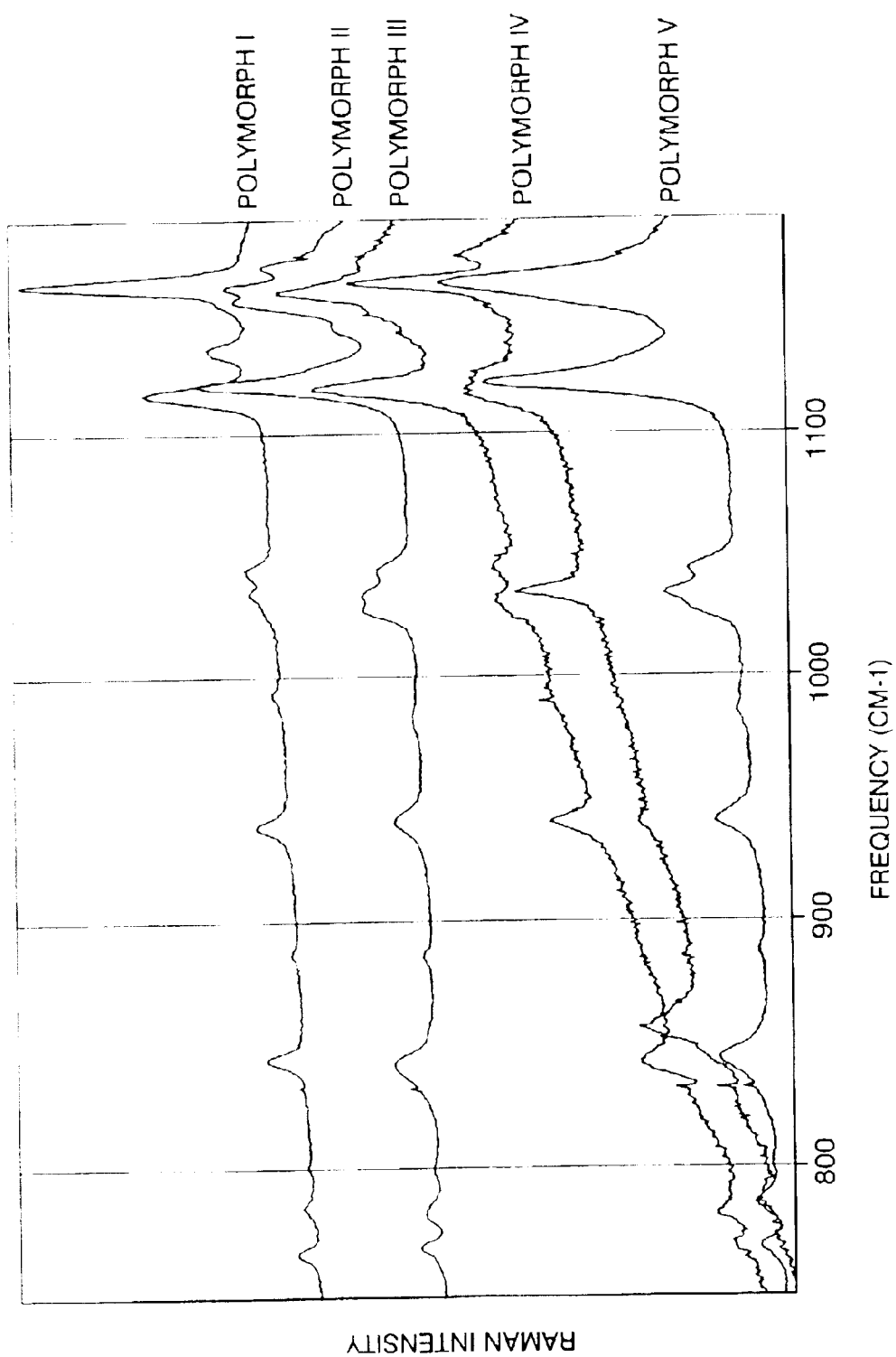
Figure 14:
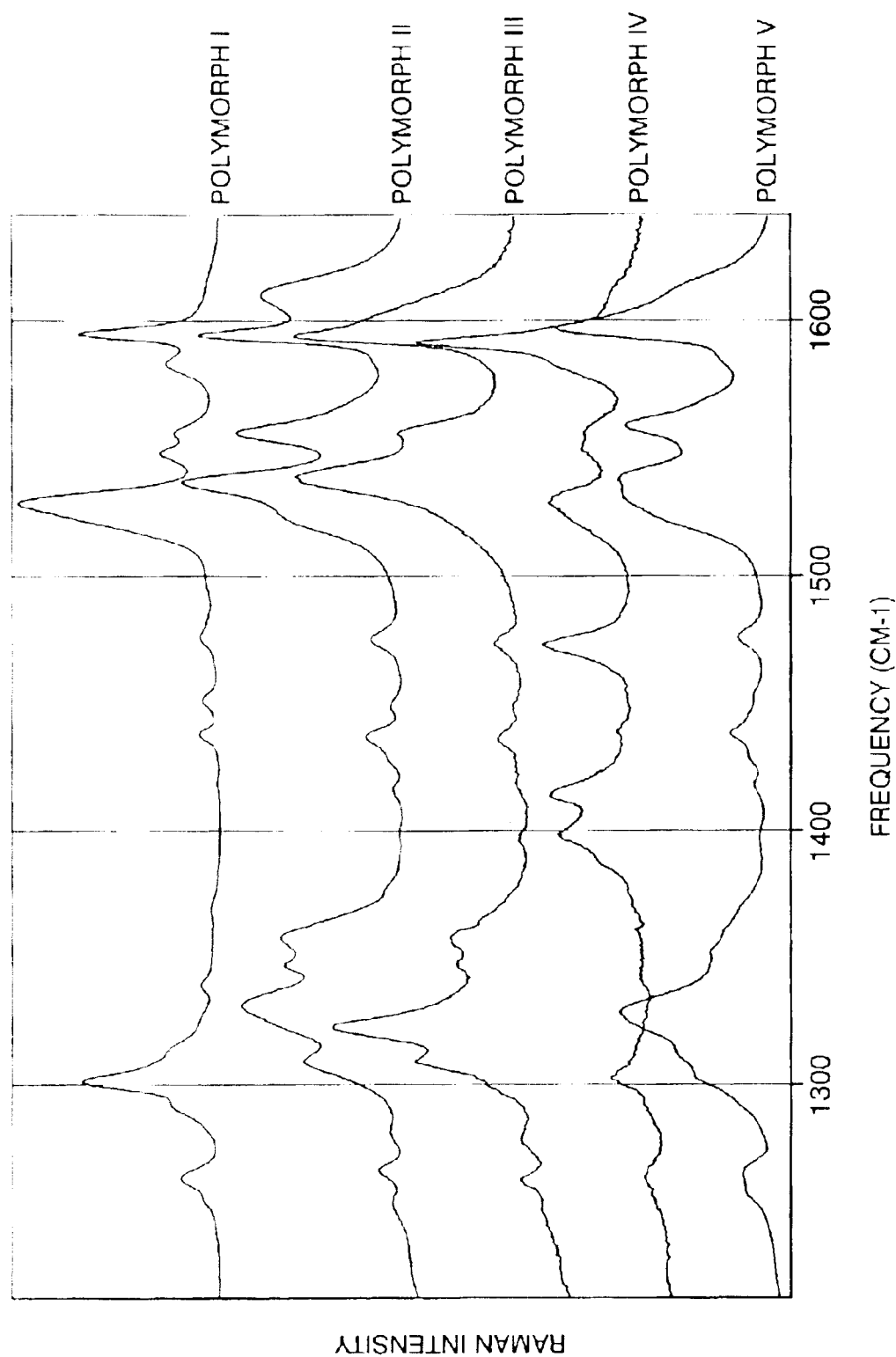

The crystalline form V of meloxicam is characterised by the following values of its infrared spectrum (see FIG. 5):

IR (KBr): v 3110, 2942, 2919, 2879, 2858, 1623, 1600, 1549, 1522, 1458, 1402, 1351, 1323, 1301, 1277, 1267, 1221, 1183, 1153, 1066, 1042, 985, 964, 939, 846, 804, 783, 763, 731, 697, 645, 609, 574, 566, 528, 503, 452 cm$^{-1}$;
by the values of its Raman spectrum (see FIGS. 11–14):

16 (vs), 31 (sh), 47 (sh), 408 (m), 1119 (m), 1159 (m) 1261 (m), 1309 (s), 1323 (vs), 1357 (s), 1540 (vs), 1595 (vs).
and by the X-ray diffractogram of FIG. 10.

The method for preparing the crystalline form V of meloxicam involves carrying out the following stages:
 a) dissolving meloxicam in a mixture of water, NaOH at 40–45° C., with a ratio of water/meloxicam (v(ml)/p(g)) under 30 ml,
 b) adding an acid for 30 a 90 minutes until obtaining a pH of 3–5.5 maintaining the temperature of stage a), c) cooling and isolating the precipitate, and d) drying the precipitate in a vacuum at a temperature of 50 to 70° C., preferably 55 to 65° C., for 1 to 24 hours, preferably 18 to 22 hours.

The mixture of water and NaOH used in the method for preparation of the crystalline form V of meloxicam contains preferably 1 to 1.5 equivalents of NaOH with respect to meloxicam. The acid added in stage b) is preferably acetic acid.

As mentioned before, the third aspect of the invention consists of methods for converting the crystalline forms II, III, IV and V of meloxicam into the form I of said compound.

The method for converting the crystalline form II of meloxicam into the form I involves the following stages:

a) preparing a suspension of the form II of meloxicam in water, b) heating the suspension to a temperature between 50° C. and reflux temperature, and stirring at this temperature for 1 to 12 hours, and c) cooling and isolating the precipitate.

Two methods have been developed for converting the crystalline form III of meloxicam into the form I. The first of these involves the following stages:

a) preparing a suspension of the form III of meloxicam in water, b) heating the suspension to a temperature between 65° C. and reflux temperature, preferably 70° C., and stirring at this temperature for 12 to 24 hours, and c) cooling and isolating the precipitate.

The second method for converting the crystalline form III of meloxicam into the form I involves the following stages:

a) preparing a suspension of the form III of meloxicam in an alcohol, preferably methanol, ethanol or isopropanol, b) heating to reflux for 1 to 24 hours, preferably from 4 to 12 hours, and c) isolating the precipitate.

The method for converting the crystalline form IV of meloxicam into the form I involves the stages:

a) preparing a suspension of the form IV of meloxicam in water, b) heating the suspension to a temperature between 50° C. and reflux temperature, and stirring at this temperature for 1 to 24 hours, and c) cooling and isolating the precipitate.

Finally, the method for converting the crystalline form V of meloxicam into the form I involves the stages:

a) preparing a suspension of the form V of meloxicam in water or in an organic solvent, with this organic solvent preferably being an alcohol, such as for example isopropanol, toluene or tetrahydrofuran.

b) heating the suspension to a temperature between 50° C. and reflux temperature, and stirring at this temperature for 1 to 12 hours, and c) cooling and isolating the precipitate.

The following examples are provided only for purposes of illustration of the present invention.

EXAMPLE 1

Preparation of the Form I at 65° C.

In a glass reactor of 700 ml volume, provided with mechanical stirring by Teflon paddles, reflux coolant, thermometer and addition funnel are loaded 450 ml of water, 2.04 g (1.2 eq) of NaOH scales and 15 g of meloxicam. The mixture is heated to 65° C. with a thermostated bath. Then are added during 1 hour 4.8 g of 80% acetic acid (1.5 eq) in 100 ml of treated water. When addition has finished it is cooled to ambient temperature. The precipitate is filtered and washed with 2×15 ml of water. 14.2 g of meloxicam are obtained (yield: 96,8%). The isolated product corresponds to the form I.

EXAMPLE 2

Preparation of the Form I at 80° C.

In a glass reactor of 500 ml volume, provided with mechanical stirring by Teflon paddles, reflux coolant, thermometer and addition funnel of 10 ml volume, are loaded 250 ml of water, 2.04 g (1.2 eq) of NaOH scales and 15 g of meloxicam. The mixture is heated to 80° C. with a thermostated bath until all of the product has dissolved. Then are added during 1 hour 4.8 g of 80% acetic acid (1.5 eq). It is maintained for 45 min to 1 hour at 80° C. and then cooled to ambient temperature. It is filtered and washed with 2×20 ml of water. 14.93 g of meloxicam are obtained (yield: 99.5%). The isolated product corresponds to the form I.

EXAMPLE 3

Preparation of the Form I at 100° C.

In a glass reactor of 700 ml volume, provided with mechanical stirring by Teflon paddles, reflux coolant, thermometer and addition funnel are loaded 450 ml of water, 2.04 g (1.2 eq) of NaOH scales and 15 g of meloxicam. The mixture is heated to 100° C. with a thermostated bath. Then are added during 1 hour 4.8 g of 80% acetic acid (1.5 eq) When addition has finished it is cooled to ambient temperature. The precipitate is filtered and washed with 2×15 ml of water. 14.44 g of meloxicam are obtained (yield: 96.3%). The isolated product corresponds to the form I.

EXAMPLE 4

Preparation of the Form I at 80° C. with 35% Hydrochloric Acid

In a glass reactor of 700 ml volume, provided with mechanical stirring by Teflon paddles, reflux coolant, thermometer and addition funnel are loaded 450 ml of water, 2.04 g (1.2 eq) of NaOH scales and 15 g of meloxicam. The mixture is heated to 80° C. with a thermostated bath. Then are added during 1 hour 5.34 g of 35% hydrochloric acid (1.2 eq). When addition has finished (pH=5.5) the mixture is cooled to ambient temperature. The precipitate is filtered and washed with 2×15 ml of water. 14.42 g of meloxicam are obtained (yield: 96%). The isolated product corresponds to the form I.

EXAMPLE 5

Preparation of the Form I at 80° C. with Methansulphonic Acid

In a glass reactor of 700 ml volume, provided with mechanical stirring by Teflon paddles, reflux coolant, thermometer and addition funnel are loaded 450 ml of water, 2.05 g (1.2 eq) of NaOH scales and 15 g of meloxicam. The mixture is heated to 80° C. with a thermostated bath. Then are added during 1 hour a solution of 4.92 g of methansulphonic acid (1.2 eq) in 10 ml of water. When addition has finished (pH=5.0) the mixture is cooled to ambient temperature. The precipitate is filtered and washed with 2×15 ml of water. 14.32 g of meloxicam are obtained (yield: 95%). The isolated product corresponds to the form I.

EXAMPLE 6

Preparation of the Form I at 70° C. in a 10:1 Water/Ethanol Mixture

In a glass reactor of 700 ml volume, provided with mechanical stirring by Teflon paddles, reflux coolant, thermometer and addition funnel are loaded 250 ml of water, 2.04 g (1.2 eq) of NaOH scales and 15 g of meloxicam. The mixture is heated to 70° C. with a thermostated bath and 25 ml of ethanol are added. Then are added for 1 hour 4.8 g of 80% acetic acid (1.5 eq). When addition has finished it is cooled to ambient temperature. The precipitate is filtered and washed with 2×15 ml of water. 14.24 g of meloxicam are obtained (yield: 95%). The isolated product corresponds to the form I.

EXAMPLE 7

Preparation of the Form I at 50° C. in a 1:1 Ethanol/Water Mixture

In a glass reactor of 700 ml volume, provided with mechanical stirring by Teflon paddles, reflux coolant, thermometer and addition funnel are loaded 200 ml of water, 2.04 g (1.2 eq) of NaOH scales, 15 g of meloxicam and 200 ml of ethanol. The mixture is heated to 50° C. with a thermostated bath. Then are added during 1 hour 4.8 g of 80% acetic acid (1.5 eq). When addition has finished it is cooled to 0/5° C. The precipitate is filtered and washed with 2×15 ml of treated water. 14.16 g of meloxicam are obtained (yield: 94%). The isolated product corresponds to the form I.

EXAMPLE 8

Preparation of the Form I at 63° C. in a 1:1 DMF/Water Mixture

In a glass reactor of 700 ml volume, provided with mechanical stirring by Teflon paddles, reflux coolant, thermometer and addition funnel are loaded 184 ml of water, 2.04 g (1.2 eq) of NaOH scales, 15 g of meloxicam and 184 ml of DMF. The mixture is heated to 63° C. with a thermostated bath. Then are added during 1 hour 4.8 g of 80% acetic acid (1.5 eq). When addition has finished The mixture is maintained at 63° C. for 1 h and then it is cooled to 0/5° C. The precipitate is filtered and washed with 2×15 ml of water. 13.12 g of meloxicam are obtained (yield: 87%). The isolated product corresponds to the form I.

EXAMPLE 9

Preparation of the Form I at 50° C. in a 8:1 Water/DMF Mixture

In a glass reactor of 500 ml volume, provided with mechanical stirring by Teflon paddles, reflux coolant, thermometer and addition funnel, are loaded 250 ml of water, 2.04 g (1.2 eq) of NaOH scales, 15 g of meloxicam and 30 ml of dimethylformamide (DMF). The mixture is heated to 50° C. with a thermostated bath. Then are added during 1 hour 4.8 g of 80% acetic acid (1.5 eq) in 50 ml of treated water. When addition has finished the mixture is kept with stirring for 2 h. It is cooled to ambient temperature. The precipitate is filtered and washed with 2×15 ml of water. 14.53 g of meloxicam are obtained (yield: 97%). The isolated product corresponds to the form I.

EXAMPLE 10

Preparation of the Crystalline Form II

In a glass reactor of 10 l volume provided with mechanical stirring by stainless steel paddles and a thermometer are loaded 9 liters of water and 41 g (1.2 eq) of NaOH scales, then adding 300 g of meloxicam. The mixture is heated to 50° C. and 3 g are added of DAB-VI carbon, and after 20 min it is filtered and washed with 1 l of treated water. Maintaining the filtrate temperature between 45–50° C. a solution is added of 192 g of 80% acetic acid (3 eq) in 3 l of water. When addition has finished, the suspension is maintained for one hour at 45–50° C. and afterwards it is cooled to ambient temperature. It is filtered, washed with 3 litres of water and dried. 288.6 g of meloxicam are obtained (yield: 96%). The isolated product corresponds to the crystalline form II.

EXAMPLE 11

Preparation of the Crystalline Form III

In a glass reactor with 500 ml volume, provided with mechanical stirring by Teflon paddles, reflux coolant, thermometer and addition funnel of 10 ml volume, are loaded 250 ml of water, 2.04 g (1.2 eq) of NaOH scales, 15 g of meloxicam and 2 ml de xylene (ca. 10% b/w). The suspension is heated to 50° C. in a thermostated bath until all the product has dissolved. Then are added during 1 hour, 4.8 g (1.5 eq) of 80% acetic acid. When addition has finished, the suspension is cooled to ambient temperature, the solid obtained is filtered and washed with 2×20 ml of water. 14.71 g of meloxicam are obtained (yield: 98%). The isolated product corresponds to the form III.

EXAMPLE 12

Preparation of the Crystalline Form V

In a glass reactor with 500 ml volume, provided with mechanical stirring by Teflon paddles, reflux coolant, thermometer and addition funnel are loaded 300 ml of water, 1.35 g (1.2 eq) of NaOH scales and 10 g of meloxicam. The mixture is heated to 50° C. with a thermostated bath. Then are added during 1 hour 3.5 g of 80% acetic acid (1.5 eq) in 7 ml of water. When addition has finished, it is cooled to ambient temperature. The precipitate is filtered and washed with 70 ml of treated water. The solid obtained is dried at 60° C. in a vacuum. After 21 h 9.43 g of meloxicam are obtained (yield: 94%). The isolated product corresponds to the form V.

EXAMPLE 13

Transformation of the Form II into the Form I by Digestion with Water at 50° C.

In a glass reactor of 500 ml volume, provided with mechanical stirring by stainless steel paddles, reflux coolant and a thermometer, are loaded 250 ml of water and 50 g of meloxicam form II. The suspension is heated to 50° C. After 1.5 hours it is cooled, filtered and washed with 50 ml of water. It is dried at 60° C. in a vacuum providing 48.17 g (yield: 96%) of meloxicam form I.

EXAMPLE 14

Transformation of the Form III into the Form I in Water

In a balloon of 50 ml volume with magnetic stirring and reflux coolant are placed 5 g of meloxicam form III and 25 ml of water. It is heated to 70° C. and maintained thus overnight. Then it is cooled to ambient temperature, filtered and dried at 60° C. in a vacuum to obtain 3.68 g (yield: 74%) of meloxicam form I.

EXAMPLE 15

Transformation of the Form III into the Form I by Digestion in Methanol

In a balloon of 50 ml volume with magnetic stirring and reflux coolant, are placed 5 g of meloxicam form III and 25 ml of methanol. It is heated to reflux (dissolving partially) for approximately 1.5 h; it is then cooled to ambient temperature, filtered and washed with 5 ml of methanol. It is dried at 60° C. with a vacuum to obtain 4.65 g (yield: 93%) of meloxicam form I.

EXAMPLE 16

Transformation of the Form III into the Form I by Digestion in IPA

In a balloon of 100 ml volume, with magnetic stirring and reflux coolant, are placed 5 g of meloxicam form III and 50 ml of isopropanol. It is heated to reflux and this maintained for 1 hour. Then it is cooled, filtered and washed with 5 ml of IPA. It is dried at 60° C. with a vacuum and 4.86 g are obtained (yield: 97%) of meloxicam form I.

EXAMPLE 17

Transformation of the Crystalline Form IV into the Form I

In a balloon of 100 ml volume, with magnetic stirring and reflux coolant, are placed 5 g of meloxicam form IV and 50 ml of water, it is heated and maintained ½ hour at 50° C. and 1 hour at 60° C. Afterwards it is cooled to ambient temperature and filtered. The solid obtained is dried at 60° C. with a vacuum and 4.22 g are obtained (yield: 84%) of meloxicam form I.

EXAMPLE 18

Transformation of the Crystalline Form V into the Form I in Isopropanol

In a balloon of 50 ml volume, with magnetic stirring and reflux coolant are placed 5 g of meloxicam form V and 25 ml of isopropanol. It is heated at 50° C. for approximately 1 h, then cooled to ambient temperature, filtered and washed with 5 ml of isopropanol. It is dried at 60° C. with a vacuum and 4.53 g are obtained (yield: 91%) of meloxicam form I.

EXAMPLE 19

Transformation of the Crystalline Form V into the Form I in Water

In a balloon of 50 ml volume, with magnetic stirring and reflux coolant are placed 5 g of meloxicam form V and 25 ml of water. It is heated at 50° C. for approximately 2 h, then cooled to ambient temperature, filtered and washed with 5 ml of water. It is dried at 60° C. with a vacuum and 4.3 g are obtained (yield: 86%) of meloxicam form I.

What is claimed is:

1. Crystalline form II of meloxicam characterized by having the following values of its infrared spectrum: IR (KBr): V 3104, 2974, 2927, 2880, 2858, 1620, 1603, 1549, 1523, 1455, 1417, 1403, 1349, 1303, 1289, 1270, 1240, 1221, 1182, 1156, 1127, 1119, 1066, 1042, 939, 856, 842, 807, 779, 762, 731, 693, 644, 609, 574, 565, 531, 504, 454 cm$^{-1}$;

the following values of its Raman spectrum:
20 (vs), 31 (s), 73 (m), 100 (s), 371 (m), 407 (s), 506 (m), 646 (m), 668 (m), 1121 (s), 1128 (sh), 1155 (s) 1161 (s), 1267 (s), 1310 (vs), 1333 (vs), 1347 (vs), 1359 (vs), 1438 (s), 1476 (s), 1538 (vs), 1557 (vs), 1595 (vs), 1611 (vs);

and the following X-ray diffractogram of FIG. 7.

2. Crystalline form III of meloxicam characterised by having the following values of its infrared spectrum: IR (KBr): V 3128, 2979, 2944, 2921, 1615, 1595, 1552, 1518, 1457, 1396, 1348, 1324, 1301, 1285, 1264, 1237, 1220, 1181, 1152, 1140, 1130, 1118, 1064, 1043, 992, 937, 860, 840, 807, 781, 758, 730, 688, 641, 607, 573, 565, 533, 523, 502, 454 cm$^{-1}$; the following values of its Raman spectrum: 27 (s), 37 (s), 48 (s), 63 (s), 97 (m), 407 (s), 1119 (m), 1159 (m), 1261 (m), 1309 (s), 1323 (vs), 1357 (s) 1540 (vs), 1595 (vs); and the following X-ray diffractogram of FIG. 8.

3. Crystalline form V of meloxicam characterised by having the following values of its infrared spectrum:
IR (KBr): v 3110, 2942, 2919, 2879, 2858, 1623, 1600, 1549, 1522, 1458, 1402, 1351, 1323, 1301, 1277, 1267, 1221, 1183, 1153, 1066, 1042, 985, 964, 939, 846, 804, 783, 763, 731, 697, 645, 609, 574, 566, 528, 503, 452 cm$^{-1}$ the following values of its Raman spectrum: 16 (vs), 31 (sh), 47 (sh), 408 (m), 1119 (m), 1159 (m) 1261 (m), 1309 (s), 1323 (vs), 1357 (s), 1540 (vs), 1595 (vs) and the following X-ray diffractogram of FIG. 10.

4. Method for preparation of the crystalline form I of meloxicam, represented by the Formula A:

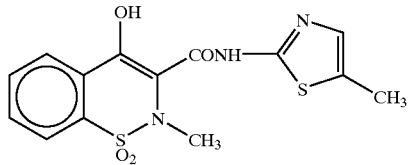

that involves dissolving meloxicam in a mixture consisting of water and NaOH, and subsequent addition of an acid for precipitation of the crystalline form I of meloxicam, maintaining throughout the process a temperature between 65° C. and the reflux temperature.

5. Method for preparation of the crystalline form I of meloxicam represented by Formula A:

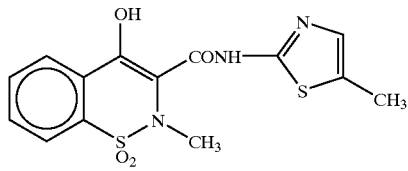

that involves dissolving meloxicam in a mixture consisting of water, NaOH and an organic solvent selected from among: an alcohol, xylene, toluene and dimethylformamide (DMF), and wherein the temperature maintained throughout the process is between 50° C. to the reflux temperature.

6. Method for preparation of the crystalline form I of meloxicam according to claim 4, comprised of the following stages:
   a) Dissolving meloxicam in a mixture consisting of water and NaOH, at a temperature between 65° C. and the reflux temperature,
   b) Adding an acid until obtaining a pH of 3 to 5.5; and
   c) cooling and isolating the precipitate.

7. Method for preparation of the crystalline form I of meloxicam according to claim 5, comprised of the following stages:
   a) Dissolving meloxicam in a mixture consisting of water, NaOH and an organic solvent selected from among: an alcohol, xylene, toluene and dimethylformamide (DMF), at a temperature between 50° C. and the reflux temperature,
   b) Adding an acid until obtaining a pH of 3 to 5.5; and
   c) cooling and isolating the precipitate.

8. Method for preparation of the crystalline form I of meloxicam according to claims 4 or 6, wherein the process temperature is between 65° C. and 80° C.

9. Method for preparation of the crystalline form I of meloxicam according to claims 5 or 7, wherein the process temperature is between 50° C. and 80° C.

10. Method for preparation of the crystalline form I of meloxicam according to claims 5 or 7, wherein the organic solvent used is xylene in a water/xylene ratio of 12.5:1 (v/v).

11. Method for preparation of the crystalline form I of meloxicam according to claims 5 or 7, wherein the organic solvent used is dimethylformamide in a water/DMF ratio of 1:1 to 8:1 (v/v).

12. Method for preparation of the crystalline form I of meloxicam according to claims 5 or 7, wherein the alcohol used is ethanol in a water/ethanol ration of 1:1 to 10:1 (v/v).

13. Method for preparation of the crystalline form I of meloxicam according to claims 4, wherein the acid that is added is acetic acid.

14. Method for preparation of the crystalline form I of meloxicam according to claim 4, wherein the process temperature is between 65° C. and 80° C.

15. Method for preparation of the crystalline form I of meloxicam according to claim 7, wherein the process temperature is between 50° C. and 80° C.

16. Method for preparation of the crystalline form I of meloxicam according to claim 7, wherein the organic solvent used is xylene in a water/xylene ratio of 12.5:1 (v/v).

17. Method for preparation of the crystalline form I of meloxicam according to claim 7, wherein the organic solvent used is dimethylformamide in a water/DMF ratio of 1:1 to 8:1 (v/v).

18. Method for preparation of the crystalline form I of meloxicam according to claim 7, wherein the alcohol used is ethanol in a water/ethanol ratio of 1:1 to 10:1 (v/v).

19. Method for preparation of the crystalline form II of meloxicam that involves carrying out the following stages:
 a) dissolving meloxicam in a mixture of water and NaOH at 45–50°C., with a water/meloxicam ratio (v(ml)/p(g)) of 30 to 35,
 b) adding an acid until obtaining a pH of 3 to 5.5, maintaining the temperature of stage a)
 c) maintaining the suspension at the temperature of stage a) for 30 to 90 minutes, and
 d) cooling and isolating the precipitate.

20. Method for preparation of the crystalline form II of meloxicam according to claim 18, wherein the acid that is added is acetic acid.

21. Method for preparation of the crystalline form III of meloxicam that involves carrying out the following stages:
 a) dissolving meloxicam in a mixture of water, NaOH and xylene at 45–50° C., with the concentration of meloxicam being 15 to 20 ml of water/g of meloxicam and the concentration of xylene being 5 to 10% by weight with respect to meloxicam,
 b) adding an acid for 30 to 90 minutes until obtaining a pH of 3 to 5.5, maintaining the temperature of stage a), and
 c) cooling and isolating the precipitate.

22. Method for preparation of the crystalline form III of meloxicam according to claim 20, wherein the acid that is added is acetic acid.

23. Method for preparation of the crystalline form V of meloxicam that involves carrying out the following stages:
 a) dissolving meloxicam in a mixture of water, NaOH at 40–45° C., with a water/meloxicam ratio (v(ml)/p(g)) under 30 ml,
 b) adding an acid for 30 to 90 minutes until obtaining a pH of 3 to 5.5, maintaining the temperature of stage a)
 c) cooling and isolating the precipitate, and
 d) drying the precipitate in a vacuum at a temperature of 50 to 70° C. for 1 to 24 hours.

24. Method for preparation of the crystalline form V of meloxicam according to claim 22, wherein the acid that is added is acetic acid.

25. Method for converting the crystalline form II of meloxicam into the form I that involves carrying out the following stages:
 a) preparing a suspension of the form II of meloxicam in water,
 b) heating the suspension to a temperature between 50° C. and reflux temperature, and stirring at this temperature for 1 a 12 hours, and
 c) cooling and isolating the precipitate.

26. Method for converting the crystalline form III of meloxicam into the form I that involves carrying out the following stages:
 a) preparing a suspension of the form III of meloxicam in water,
 b) heating the suspension to a temperature between 65° C. and reflux temperature, and stirring at this temperature for 12 a 24 hours, and
 c) cooling and isolating the precipitate.

27. Method for converting the crystalline form III of meloxicam into the form I that involves carrying out the following stages:
 a) preparing a suspension of the form III of meloxicam in an alcohol,
 b) heating to reflux for 1 to 12 hours, and
 c) cooling and isolating the precipitate.

28. Method for converting the crystalline form III of meloxicam into the form I according to claim 26 wherein the alcohol used is methanol, ethanol or isopropanol.

29. Method for converting the crystalline form IV of meloxicam into the form I that involves carrying out the following stages:
 a) preparing a suspension of the form IV of meloxicam in water,
 b) heating the suspension to a temperature between 50° C. and reflux temperature, and stirring at this temperature for 1 to 24 hours, and
 c) cooling and isolating the precipitate.

30. Method for converting the crystalline form V of meloxicam into the form I that involves carrying out the following stages:
 a) preparing a suspension of the form V of meloxicam in water or an organic solvent,
 b) heating the suspension to a temperature between 50° C. and reflux temperature, and stirring at this temperature for 1 to 12 hours, and
 c) isolating the precipitate.

31. Method for converting the crystalline form V of meloxicam into the form I according to claim 29 wherein the organic solvent is isopropanol.

32. Method for converting the crystalline form V of meloxicam into the form I according to claim 29 wherein the organic solvent is toluene.

33. Method for converting the crystalline form V of meloxicam into the form I according to claim 29 wherein the organic solvent is tetrahydrofuran (THF).

* * * * *